US012582693B2

(12) United States Patent  
Ichinose et al.

(10) Patent No.: US 12,582,693 B2  
(45) Date of Patent: Mar. 24, 2026

(54) GLUTATHIONE TRISULFIDE (GSSSG) IN NEUROPROTECTION

(71) Applicant: The General Hospital Corporation, Boston, MA (US)

(72) Inventors: Fumito Ichinose, Chestnut Hill, MA (US); Eizo Marutani, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 680 days.

(21) Appl. No.: 17/924,622

(22) PCT Filed: May 11, 2021

(86) PCT No.: PCT/US2021/031842
§ 371 (c)(1),
(2) Date: Nov. 10, 2022

(87) PCT Pub. No.: WO2021/231476

PCT Pub. Date: Nov. 18, 2021

(65) Prior Publication Data

US 2023/0181676 A1     Jun. 15, 2023

Related U.S. Application Data

(60) Provisional application No. 63/023,686, filed on May 12, 2020.

(51) Int. Cl.
| | |
|---|---|
| *A61K 38/06* | (2006.01) |
| *A61P 25/00* | (2006.01) |
| *A61P 25/28* | (2006.01) |

(52) U.S. Cl.
CPC ............ *A61K 38/063* (2013.01); *A61P 25/00* (2018.01); *A61P 25/28* (2018.01)

(58) Field of Classification Search
CPC ...... A61K 38/063; A61K 9/0019; A61K 9/08; A61K 47/20; A61P 25/00; A61P 25/28; C07K 5/0215; C07K 5/0606; C07K 5/0819
See application file for complete search history.

(56) References Cited

U.S. PATENT DOCUMENTS

| | | |
|---|---|---|
| 9,249,517 B2 | 2/2016 | Fukumoto |
| 2013/0252897 A1 | 9/2013 | Roth et al. |
| 2018/0296504 A1 | 10/2018 | Nakazawa et al. |
| 2020/0079818 A1 | 3/2020 | Fujimoto et al. |
| 2020/0268692 A1 | 8/2020 | Stanton, Jr. et al. |

FOREIGN PATENT DOCUMENTS

| | | |
|---|---|---|
| EP | 3560947 | 10/2019 |
| WO | WO 1989/000427 | 1/1989 |
| WO | WO 2017/057768 A1 | 4/2017 |

| | | |
|---|---|---|
| WO | WO 2018/117186 A1 | 6/2018 |
| WO | WO 2018/207879 | 11/2018 |
| WO | WO 2020/158894 | 8/2020 |
| WO | WO 2021/231476 | 11/2021 |
| WO | WO 2022/045052 | 3/2022 |
| WO | WO 2022/045212 | 3/2022 |
| WO | WO 2023/225305 | 11/2023 |

OTHER PUBLICATIONS

Extended European Search Report in European Appln. No. 21804146. 5, dated Mar. 25, 2024, 9 pages.
Office Action in Japanese Appln. No. 2022-568697, mailed on Mar. 25, 2025, 8 pages (with English translation).
International Preliminary Report on Patentability in International Appln. No. PCT/US2023/022917, mailed on Dec. 5, 2024, 8 pages.
Akaike et al., "Cysteinyl-tRNA synthetase governs cysteine polysulfidation and mitochondrial bioenergetics," Nature Communications, Oct. 2017, 8(1):1177, 15 pages.
Aquilano et al., "Glutathione: new roles in redox signaling for an old antioxidant," Front Pharmacol, Aug. 2014, 5:196, 12 pages.
Awad et al., "A mouse model of ischemic spinal cord injury with delayed paralysis caused by aortic cross-clamping," Anesthesiology, Oct. 2010, 113(4):880-91.
Baranger et al., "Long-Term Pantethine Treatment Counteracts Pathologic Gene Dysregulation and Decreases Alzheimer's Disease Pathogenesis in a Transgenic Mouse Model," Neurotherapeutics, Oct. 2019, 16(4): 1237-1254.
Barayeu et al., "Abstract: Antioxidative and cytoprotective properties of sulfane sulfur species," Abstract, Presented at Proceedings of the Free radicals in chemistry and life III International Conference, Heidelberg, Germany, Oct. 10-11, 2019, 1 page.
Barayeu et al., "Hydropersulfides inhibit lipid peroxidation and ferroptosis by scavenging radicals," Nat Chem Biol, Jan. 2023, 19(1):28-37, 27 pages.
Bartanusz et al., "The blood-spinal cord barrier: morphology and clinical implications," Ann Neurol, Aug. 2011, 70(2): 194-206.
Basso et al., "Basso Mouse Scale for locomotion detects differences in recovery after spinal cord injury in five common mouse strains," J Neurotrauma, May 2006, 23(5):635-659.
Bell et al., "Toll-Like Receptor 4-Dependent Microglial Activation Mediates Spinal Cord Ischemia-Reperfusion Injury," Circulation, Sep. 2013, 128:S152-S156, 13 pages.
Bianco et al., "The reaction of hydrogen sulfide with disulfides: formation of a stable trisulfide and implications for biological systems," Br J Pharmacol, Feb. 2019, 176(4):671-683.

(Continued)

*Primary Examiner* — Olga N Chernyshev
(74) *Attorney, Agent, or Firm* — Fish & Richardson P.C.

(57) ABSTRACT

Methods for the use of glutathione trisulfide (GSSSG) in neuroprotection, e.g., in neurodegenerative diseases and to reduce the risk of ischemic injury. The methods can be used, e.g., to reduce risk of injury to brain, spinal cord, and peripheral nerves from ischemia or low blood flow states possibly caused by surgery, trauma, and other conditions that decrease/impair blood flow and or oxygen delivery to the nervous system.

5 Claims, 2 Drawing Sheets

(56)                    References Cited

OTHER PUBLICATIONS

Braunstein et al., "Opposing effects of polysulfides and thioredoxin on apoptosis through caspase persulfidation," J Biol Chem, Mar. 2020, 295(11):3590-3600.

Brunetti et al., "Pantethine treatment is effective in recovering the disease phenotype induced by ketogenic diet in a pantothenate kinase-associated neurodegeneration mouse model, " Brain, Jan. 2014, 137(Pt 1):57-68.

Cha et al., "Protein Glutathionylation in the Pathogenesis of Neurodegenerative Diseases," Oxidative Medicine and Cellular Longevity, 2017, 2017:2818565, 10 pages.

Chiang et al., "Relationships among Cortical Glutathione Levels, Brain Amyloidosis, and Memory in Healthy Older Adults Investigated In Vivo with $^1$H-MRS and Pittsburgh Compound-B PET," AJNR Am J Neuroradiol, Jun. 2017, 38(6):1130-1137.

Dénes et al., "Role of CX3CR1 (fractalkine receptor) in brain damage and inflammation induced by focal cerebral ischemia in mouse," J Cereb Blood Flow Metab, Oct. 2008, 28(10):1707-1721.

Dhuria et al., "Intranasal delivery to the central nervous system: mechanisms and experimental considerations," J Pharm Sci, Apr. 2010, 99(4): 1654-73.

Donnelly et al., "Deficient CX3CR1 signaling promotes recovery after mouse spinal cord injury by limiting the recruitment and activation of Ly6C$^{lo}$/iNOS+ macrophages," The Journal of Neuroscience, Jul. 2011, 31(27):9910-9922.

Etz et al., "Paraplegia after extensive thoracic and thoracoabdominal aortic aneurysm repair: does critical spinal cord ischemia occur postoperatively?," J Thorac Cardiovasc Surg, Feb. 2008, 135(2):324-30.

Faul et al., "G*Power 3: a flexible statistical power analysis program for the social, behavioral, and biomedical sciences," Behav Res Methods, May 2007, 39(2): 175-91.

Gao et al., "Resveratrol mitigates the oxidative stress mediated by hypoxic-ischemic brain injury in neonatal rats via Nrf2/HO-1 pathway," Pharm Biol, Nov. 2018, 56(1): 440-449.

Giustarini et al., "S-glutathionylation: from redox regulation of protein functions to human diseases," J Cell Mol Med, Apr. 2004, 8(2):201-12.

Hamid et al., "Polysulfide stabilization by tyrosine and hydroxyphenyl-containing derivatives that is important for a reactive sulfur metabolomics analysis," Redox Biol, Feb. 2019, 21:101096, 7 pages.

Hanson and Frey, "Intranasal delivery bypasses the blood-brain barrier to target therapeutic agents to the central nervous system and treat neurodegenerative disease," BMC Neurosci, Dec. 2008, 9 Suppl 3(Suppl 3):S5, 4 pages.

Hauser et al., "Randomized, double-blind, pilot evaluation of intravenous glutathione in Parkinson's disease," Movement Disorders, May 2009, 24(7):979-983.

Hong et al., "Liposomal Formulations for Nose-to-Brain Delivery: Recent Advances and Future Perspectives," Pharmaceutics, 2019, 11:540, 19 pages.

Ida et al., "Reactive cysteine persulfides and S-polythiolation regulate oxidative stress and redox signaling," Proceedings of the National Academy of Sciences, Apr. 2014, 111(21):7606-7611.

International Preliminary Report on Patentability in International Appln. No. PCT/US2021/031842, mailed on Nov. 24, 2022, 6 pages.

International Search Report and Written Opinion in International Appln. No. PCT/US2021/031842, mailed on Aug. 10, 2021, 7 pages.

Ito et al., "Enhanced expression of Ibal, ionized calcium-binding adapter molecule 1, after transient focal cerebral ischemia in rat brain," Stroke, May 2001, 32(5):1208-15.

Kakinohana et al., "Breathing hydrogen sulfide prevents delayed paraplegia in mice," Free Radic Biol Med., Feb. 2019, 131:243-250.

Kakinohana et al., "Delayed Paraplegia After Spinal Cord Ischemic Injury Requires Caspase-3 Activation in Mice," Stroke, Aug. 2011, 42(8):2302-7, 13 pages.

Kanemaru et al., "Intranasal administration of polysulfide prevents neurodegeneration in spinal cord and rescues mice from delayed paraplegia after spinal cord ischemia," Redox Biol., Apr. 2023, 60:102620, 13 pages.

Kasamatsu et al., "High-Precision Sulfur Metabolomics Innovated by a New Specific Probe for Trapping Reactive Sulfur Species," Antioxid Redox Signal, Jun. 2021, 34(18): 1407-1419.

Kasamatsu, "Persulfide-dependent regulation of electrophilic redox signaling in neural cells," Antioxid Redox Signal, Dec. 2020, 33(18): 1320-1331.

Kida and Ichinose, "Hydrogen Sulfide and Neuroinflammation," Handb Exp Pharmacol., 2015, 230:181-9.

Kida et al., "Inhaled hydrogen sulfide prevents neurodegeneration and movement disorder in a mouse model of Parkinson's disease," Antioxidants & Redox Signaling, Jun. 2011, 15(2):343-352.

Kigerl et al., "Toll-like receptor (TLR)-2 and TLR-4 regulate inflammation, gliosis, and myelin sparing after spinal cord injury," Journal of Neurochemistry, Jul. 2007, 102(1):37-50.

Kimura, "Signaling by hydrogen sulfide ($H_2S$) and polysulfides ($H_2S_n$) in the central nervous system," Neurochem Int, Jun. 2019, 126:118-125.

Kimura, "Signaling molecules: hydrogen sulfide and polysulfide," Antioxid Redox Signal, Feb. 2015, 22(5):362-76.

Kimura, "Signalling by hydrogen sulfide and polysulfides via protein S-sulfuration," Br J Pharmacol, Feb. 2020, 177(4):720-733.

Kunikata et al., "Metabolomic profiling of reactive persulfides and polysulfides in the aqueous and vitreous humors," Sci Rep, Feb. 2017, 7:41984, 10 pages.

Mandal et al., "Brain Glutathione Levels; A Novel Biomarker for Mild Cognitive Impairment and Alzheimer's Disease," Biological Psychiatry, Nov. 2015, 78(10):702-710, 12 pages.

Marutani et al., "A novel hydrogen sulfide-releasing N-methyl-D-aspartate receptor antagonist prevents ischemic neuronal death," J Biol Chem, Sep. 2012, 287(38):32124-35.

Marutani et al., "Cytoprotective effects of hydrogen sulfide-releasing N-methyl-D-aspartate receptor antagonists mediated by intracellular sulfane sulfur," Medicinal Chemistry Communication, Aug. 2014, 5(10):1577-1583.

Marutani et al., "Sulfide catabolismameliorates hypoxic brain injury," Nat Commun, May 2021, 12(1):3108, 19 pages.

Marutani et al., "Thiosulfate Mediates Cytoprotective Effects of Hydrogen Sulfide Against Neuronal Ischemia," J Am Heart Assoc, Nov. 2015, 4(11):e002125, 10 pages.

Mischley et al., "A randomized, double-blind phase I/IIa study of intranasal glutathione in Parkinson's disease," Mov Disord, Oct. 2015, 30(12): 1696-1701.

Mischley et al., "Central nervous system uptake of intranasal glutathione in Parkinson's disease," NPJ Parkinsons Dis, Feb. 2016, 2:16002, 6 pages.

Mischley et al., "Phase IIb Study of Intranasal Glutathione in Parkinson's Disease," J Parkinsons Dis, 2017, 7(2):289-299.

Mischley et al., "Safety survey of intranasal glutathione," J Altern Complement Med, May 2013, 19(5):459-463.

Nagashima et al., "Sulfide:quinone oxidoreductase ameliorates neurodegeneration in a murine model of Parkinson's disease," Redox Biol., Feb. 2023, 59:102562, 11 pages.

Numakura et al., "Abstract A2662: Production of Reactive Persulfide Species and Their Effects in the Lungs of Patients with COPD," Am J Resp and Crit Care Med, 2018, 197:A2662, 1 page.

Numakura et al., "Production of reactive persulfide species in chronic obstructive pulmonary disease," Thorax, Dec. 2017, 72(12): 1074-83.

Pizzorno, "Glutathione!," Integr Med (Encinitas), Feb. 2014, 13(1):8-12.

Rae and Williams, "Glutathione in the human brain: Review of its roles and measurement by magnetic resonance spectroscopy," Analytical Biochemistry, Jul. 2017, 529:127-143.

Ramassamy et al., "Oxidative Insults Are Associated with Apolipoprotein E Genotype in Alzheimer's Disease Brain," Neurobiology of Disease, Feb. 2000, 7(1):23-37.

Rassy et al., "Intranasal Methylprednisolone Effectively Reduces Neuroinflammation in Mice With Experimental Autoimmune Encephalitis," J Neuropathol Exp Neurol, Feb. 2020, 79(2):226-37.

(56)              References Cited

OTHER PUBLICATIONS

Riambau et al., "Editor's Choice—Management of Descending Thoracic Aorta Diseases: Clinical Practice Guidelines of the European Society for Vascular Surgery (ESVS)," Eur J Vasc Endovasc Surg, Jan. 2017, 53(1):4-52.

Rossi et al., "Current options for drug delivery to the spinal cord," Expert Opin Drug Deliv, Mar. 2013, 10(3):385-96.

Sadhu et al., "Glutathione Disulfide Liposomes—a Research Tool for the Study of Glutathione Disulfide Associated Functions and Dysfunctions," Biochem Biophys Rep, Sep. 2016, 7:225-229.

Sawa et al., "Enzymatic Regulation and Biological Functions of Reactive Cysteine Persulfides and Polysulfides," Biomolecules, Aug. 2020, 10(9):1245, 13 pages.

Sechi et al., "Reduced intravenous glutathione in the treatment of early Parkinson's disease," Progress in Neuropsychopharmacology and Biological Psychiatry, Oct. 1996, 20(7):1159-1170.

Singh, "Glutathione: A marker and antioxidant for aging," The Journal of Laboratory and Clinical Medicine, Dec. 2002, 140(6):380-381.

Smith et al., "Ischemic dose-response in the spinal cord: both immediate and delayed paraplegia," J Surg Res, May 2012, 174(2):238-44.

Smith et al., "The evolution of chemokine release supports a bimodal mechanism of spinal cord ischemia and reperfusion injury," Circulation, Sep. 2012, 126(11 Supppl 1):S110-7.

Sofic et al., "Reduced and oxidized glutathione in the substantia nigra of patients with Parkinson's disease," Neuroscience Letters, Aug. 1992, 142(2):128-130.

Song et al., "Glutathione suppresses cerebral infarct vol. and cell death after ischemic injury: involvement of FOXO3 inactivation and Bcl2 expression," Oxid Med Cell Longev, 2015, 2015:426069, 11 pages.

Switzer et al., "Cysteine trisulfide oxidizes protein thiols and induces electrophilic stress in human cells," Redox Biol, Nov. 2021, 47:102155, 9 pages.

Takano et al., "Development of a reversible fluorescent probe for reactive sulfur species, sulfane sulfur, and its biological application," Chem Commun (Camb), Jan. 2017, 53(6): 1064-7.

Takata et al., "Methods in sulfide and persulfide research," Nitric Oxide, Nov. 2021, 116:47-64, 47 pages.

Thorne et al., "Delivery of insulin-like growth factor-I to the rat brain and spinal cord along olfactory and trigeminal pathways following intranasal administration," Neuroscience, 2004, 127(2):481-96.

Tokuda et al., "Inhaled Hydrogen Sulfide Prevents Endotoxin-Induced Systemic Inflammation and Improves Survival by Altering Sulfide Metabolism in Mice," Antioxidants & Redox Signaling, Jul. 2012, 17(1): 11-21.

Tóth et al., "Natural Molecules and Neuroprotection: Kynurenic Acid, Pantethine and α-Lipoic Acid," Int J Mol Sci, Jan. 2021, 22(1):403, 25 pages.

Ullery et al., "Reversal of delayed-onset para paresis after revision thoracic endovascular aortic repair for ruptured thoracic aortic aneurysm," Ann Vase Surg, Aug. 2011, 25(6): 840.e19-23.

Ullery et al., "Risk factors, outcomes, and clinical manifestations of spinal cord ischemia following thoracic endovascular aortic repair," J Vasc Surg, Sep. 2011, 54(3):677-84.

Wallace and Wang, "Hydrogen sulfide-based therapeutics: exploiting a unique but ubiquitous gasotransmitter," Nat Rev Drug Discov, May 2015, 14(5):329-45.

Wang et al., "Role of hydrogen sulfide in secondary neuronal injury," Neurochem Int, Jan. 2014, 64:37-47.

Wintner et al., "A monobromobimane-based assay to measure the pharmacokinetic profile of reactive sulphide species in blood," Br J Pharmacol, Jun. 2010, 160(4):941- 57.

Xiong et al., "S-glutathionylation: from molecular mechanisms to health outcomes," Antioxid Redox Signal, Jul. 2011, 15(1):233-70.

Yabuki and Fukunaga, "Oral administration of glutathione improves memory deficits following transient brain ischemia by reducing brain oxidative stress," Neuroscience, Oct. 2013, 250:394-407.

Zhang et al., "Enhanced Cellular Polysulfides Negatively Regulate TLR4 Signaling and Mitigate Lethal Endotoxin Shock," Cell Chem Biol, May 2019, 26(5):686-98.e4.

Ziganshin et al., "Surgical management of thoracoabdominal aneurysms," Heart, Sep. 2014, 100:1577-82.

Office Action in European Appln. No. 21804146.5, mailed on Apr. 2, 2025, 6 pages.

International Search Report and Written Opinion in International Appln. No. PCT/US2023/022917, mailed Jan. 5, 2024, 12 pages.

GLUTATHIONE TRISULFIDE (GSSSG) IN NEUROPROTECTION

CLAIM OF PRIORITY

This application is a U.S. National Phase Application under 35 U.S.C. § 371 of International Patent Application No. PCT/US2021/031842, filed on May 11, 2021, which claims the benefit of U.S. Provisional Patent Application Ser. No. 63/023,686, filed on May 12, 2020. The entire contents of the foregoing are hereby incorporated by reference.

TECHNICAL FIELD

Described herein is the use of glutathione trisulfide (GSSSG) in neuroprotection, e.g., in neurodegenerative diseases and to reduce the risk of ischemic injury. The methods can be used, e.g., to reduce risk of injury to brain, spinal cord, and peripheral nerves from ischemia or low blood flow states possibly caused by surgery, trauma, and other conditions that decrease/impair blood flow and or oxygen delivery to the nervous system.

BACKGROUND

Delayed paraplegia is a devastating complication of ischemic spinal cord injury (SCI), which can occur after thoracic and/or abdominal aortic surgery and trauma to the spinal cord. While the incidence of ischemic SCI is reported to be around 3%, more than 80% present with delayed onset of symptoms (Ullery et al., 2011). Although mechanisms of delayed paraplegia are incompletely understood, studies suggest critical roles of motor neuron apoptosis (Kakinohana et al., 2011) and recruitment of microglia and bone marrow-derived macrophages (BMDM) in ischemic stroke (Denes et al., 2008) and SCI (Bell et al., 2013; Donnelly et al., 2011; Kigerl et al., 2007).

SUMMARY

Provided herein are methods for the treatment, or reduction of risk, of a disorder associated with neurodegeneration in a subject. The methods include administering a therapeutically or prophylactically effective amount of a composition prepared using crystals of Glutathione Trisulfide (GSSSG) to a subject in need thereof. In some embodiments, the methods include comprising preparing the composition comprising GSSSG by dissolving a crystalline form of GSSSG in saline at pH 3-6. Also provided are compositions comprising GSSSG for use in a method of treatment, or reduction of risk, of a disorder associated with neurodegeneration in a subject, e.g., compositions prepared by dissolving a crystalline form of GSSSG in saline at pH 3-6.

In some embodiments, the disorder is post-ischemic neuronal death.

In some embodiments, the disorder is a chronic cerebral degenerative disease, e.g., multi-infarct dementia, Alzheimer's disease, Parkinson's disease, or Lewy body dementia.

In some embodiments, the methods include administering an effective amount of a composition comprising GSSSG within a few minutes to hours after a traumatic injury occurs.

In some embodiments, the methods include administering an effective amount of a composition comprising GSSSG before a scheduled thoracic and/or abdominal aortic surgical procedure.

In some embodiments, the methods include administering an effective amount of a composition comprising GSSSG hours to days before a scheduled thoracic and/or abdominal aortic surgical procedure.

In some embodiments, the methods include administering an effective amount of a composition comprising GSSSG 2-24 hours, and/or 1, 2, 3, 4, 5, 6, and/or 7 days before the scheduled thoracic and/or abdominal aortic surgical procedure.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
FIGS. 1A-B are graphs showing BMS (A) and survival rate (B) of mice subjected to SCI after preconditioning with GSSSG or DMSO alone.
Figure 1A:
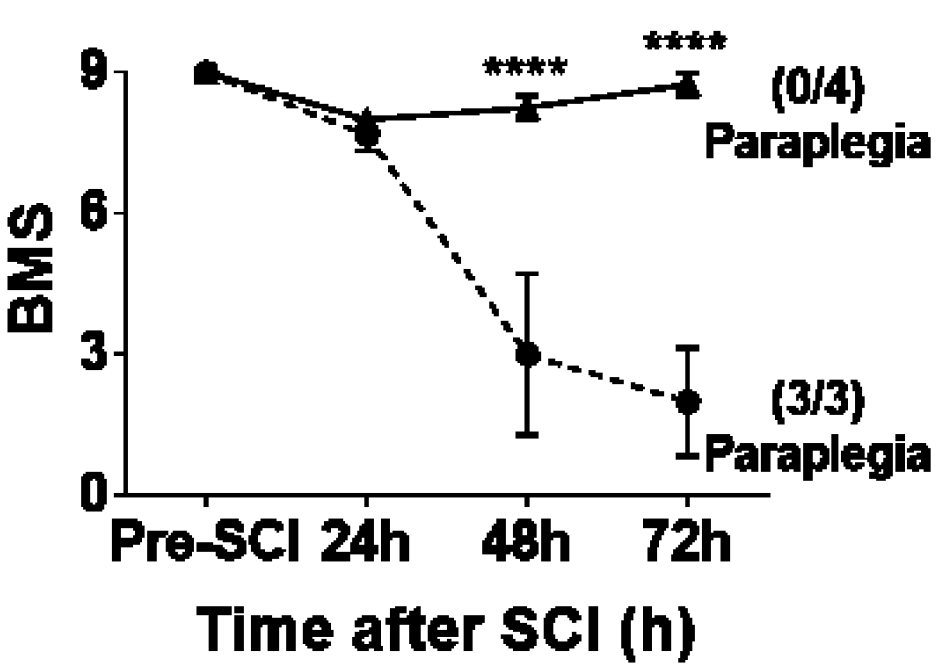

Persulfide (R—S—SH) and polysulfide (R—S—Sn—S—R) are molecules that contain sulfane sulfur which is a sulfur atom with six valence electrons but with no charge, and possess protective effects against oxidative stress (Akaike et al., 2017; Ida et al., 2014). These molecules can release $H_2S$ and, therefore, antioxidative or protective effects of these molecules seem to be mediated by both $H_2S$ and sulfane sulfur. Glutathione trisulfide (GSSSG) is one of major polysulfide species in mammal tissues that consists of GSSG, a metabolite of glutathione, with an additional sulfane sulfur atom.

Until recently, methods for manufacturing GSSG compounds included the use of toxic gases or risked the production of toxic gases, producing a compound that was not stable or not suitable for pharmaceutical use. EP 3560947 describes a method of manufacturing GSSSG in a stable crystal form. However, the efficacy of this crystal form of GSSSG in vivo for neuroprotection has not been described.

The current study examined the beneficial effects of the crystal GSSSG in neuroprotection, including against neurofunctional impairment after SCI in mice. Specifically, the effects of GSSSG preconditioning prior to SCI onset were examined. Patients often undergo aortic surgery after a certain period (e.g., 1 week) of diagnosis depending on conditions, providing an opportunity to use a treatment as described herein to reduce their risk of post-surgical complications. In addition, the results confirmed a protective effect of GSSSG against 1-methyl-4-phenylpyridinium (MPP+)-induced neuronal (SH-SY5Y cell) death. MPP+-poisoning is an in vitro model of Parkinson's disease, demonstrating that the crystal GSSSG can be used in neurodegenerative disease as well.

The results herein demonstrated the beneficial capacity of GSSSG crystal in neuroprotection in vivo. The present results showed the effects of GSSSG preconditioning on neurofunctional preservation after SCI; the drug can also be administered after onset of ischemia due to its antioxidative effects.

Methods of Treatment

The methods described herein include methods for the treatment, or reduction of risk, of disorders associated with neurodegeneration in a subject, e.g., a mammalian subject, e.g., a human or non-human veterinary subject. In some embodiments, the disorder is post-ischemic neuronal death. In some embodiments, the disorder is a chronic cerebral degenerative disease (e.g., multi-infarct dementia, Alzheimer's disease, Parkinson's disease, or Lewy body dementia). Generally, the methods include administering a therapeutically effective amount of a composition comprising a crystalline form of GSSSG as described herein, to a subject who is in need of, or who has been determined to be in need of, such treatment.

As used in this context, to "treat" means to ameliorate at least one symptom of the disorder associated with neurodegeneration. The conditions that can be treated using a method described herein can be associated with loss of motor control, paralysis or paraplegia. Administration of a therapeutically effective amount of a compound described herein can result in improved motor control, reduced paralysis or paraplegia.

In addition, the methods can result in a reduction in risk of developing loss of motor control, paralysis or paraplegia. Subjects who are at risk of developing loss of motor control, paralysis or paraplegia can include those who have suffered a traumatic injury as well as those who are about to undergo thoracic and/or abdominal aortic surgery. These methods can include administering an effective amount of a GSSSG composition as described herein within a few minutes to hours after a traumatic injury occurs, and/or before, e.g., hours to days before, a scheduled thoracic and/or abdominal aortic surgical procedure.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. The compositions can be administered one from one or more times per day to one or more times per week; including once every other day. In some embodiments, the GSSSG is administered every day for at least 2, 3, 4, 5, 6, or 7 days prior to a scheduled thoracic and/or abdominal aortic surgical procedure. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions and Methods of Administration

The methods described herein include the use of pharmaceutical compositions comprising GSSSG as an active ingredient, wherein the compositions are prepared using a crystalline form of GSSSG as described in EP 3560947, by dissolving the crystalline GSSSG in a buffer, e.g., saline, at pH 3-6. A method for producing the crystal form of glutathione trisulfide dehydrate can comprise precipitating a crystal of glutathione trisulfide dihydrate in an aqueous solution in which glutathione trisulfide is dissolved, and collecting the precipitated crystal of glutathione trisulfide dihydrate.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions are typically formulated to be compatible with its intended route of administration. Examples of routes of administration include parenteral, e.g., intravenous, administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The pharmaceutical compositions can be included in a container, pack, or dispenser together with instructions for administration. For example, the GSSSG can be provided in a kit in a crystalline form with a sterile buffer (e.g., saline) at pH 3-6 for use in dissolving the crystals to prepare a solution for injection.

EXAMPLES

The invention is further described in the following examples, which do not limit the scope of the invention described in the claims.

Example 1. Preventive Effects of GSSSG Against Neurofunctional Deficit after SCI To elucidate the molecular mechanisms responsible for the delayed paraplegia, we recently developed and thoroughly characterized a murine model of SCI in which mice exhibit delayed paraplegia with minimum operative mortality (Kakinohana et al., 2011). Briefly, under anesthesia and mechanical ventilation via endotracheal intubation, SCI was induced by placing the first clip on the aortic arch between the left common carotid artery and the left subclavian artery and the second clip on the origin of the left subclavian artery. The completeness of the occlusion was ascertained by an immediate and sustained loss of any detectable pulse pressure in the femoral artery pressure tracing. After 5 min of ischemia, the clips were removed, and the chest was closed in layers. At 10 minutes of reperfusion, the arterial catheter was removed, incisions were closed, and animals were allowed to recover from anesthesia. Temperature of erector spinae muscle was monitored and maintained at 37.5° C. during whole surgery until recovery from anesthesia. In sham-operated mice, whole surgical procedure was performed as described, but no clips were applied. Motor function was quantified serially at pre-SCI, 24, 48, and 72 h after spinal cord ischemia by the Basso Mouse Scale (BMS) (Basso et al., 2006; Kakinohana et al., 2011). The maximum deficit is indicated by a score of 0. Although BMS score<6 (0 to 5) indicates paraplegia, BMS score>6 (6 to 9) indicates ability to walk.

To examine preventive effects of GSSSG against neurofunctional deficit after SCI, mice were subjected to preconditioning with GSSSG treatment before induction of SCI. Briefly, GSSSG was ground using an agate mortar, dispersed in DMSO using a sonication water bath and administrated at 200 mg/kg IP daily for 4 days. Control mice were given DMSO alone. Mice were subjected to SCI at 24 h after the last administration of GSSSG or DMSO alone.

Figure 1B:
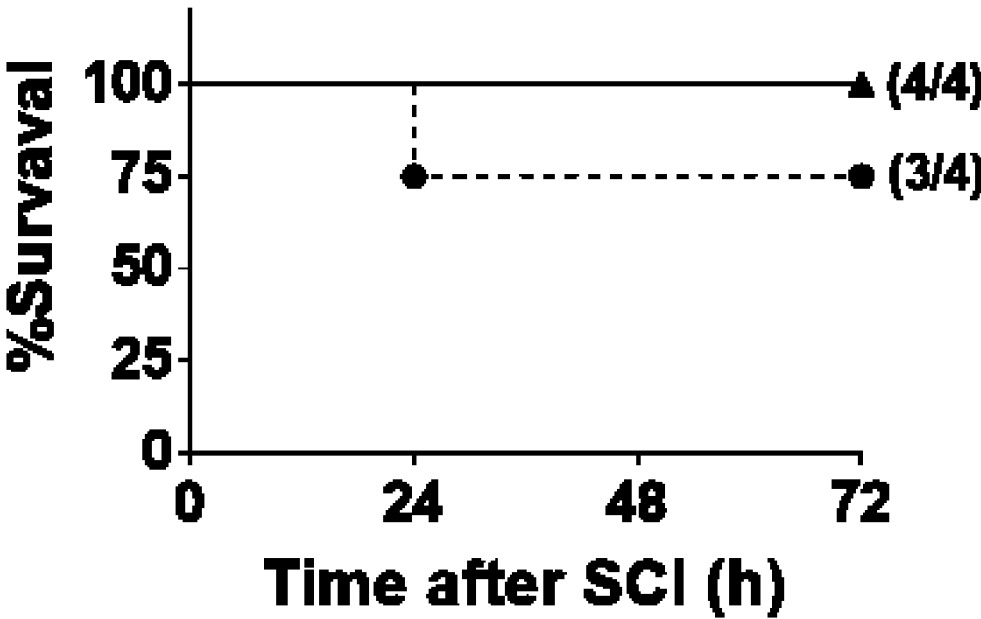

The results showed that all mice treated with DMSO alone exhibited paraplegia after SCI while preconditioning with GSSSG prevented motor functional deficit and paraplegia (FIG. 1A). Preconditioning with GSSSG did not change survival rate of mice after SCI (FIG. 1B).

Example 2. Protective Effects of GSSSG in a Model of Neurodegeneration

The effects of GSSSG on 1-methyl-4-phenylpyridinium (MPP+)-induced neuronal (SH-SY5Y cell) death were evaluated. MPP+-poisoning is an in vitro model of Parkinson's disease.

SH-SY5Y cells were incubated with or without MPP+ (2 mM) in DMEM/F12 (20% FBS) with or without drugs at 37° C. for 24 h. Cell viability was measured using the crystal violet assay.

Figure 2:
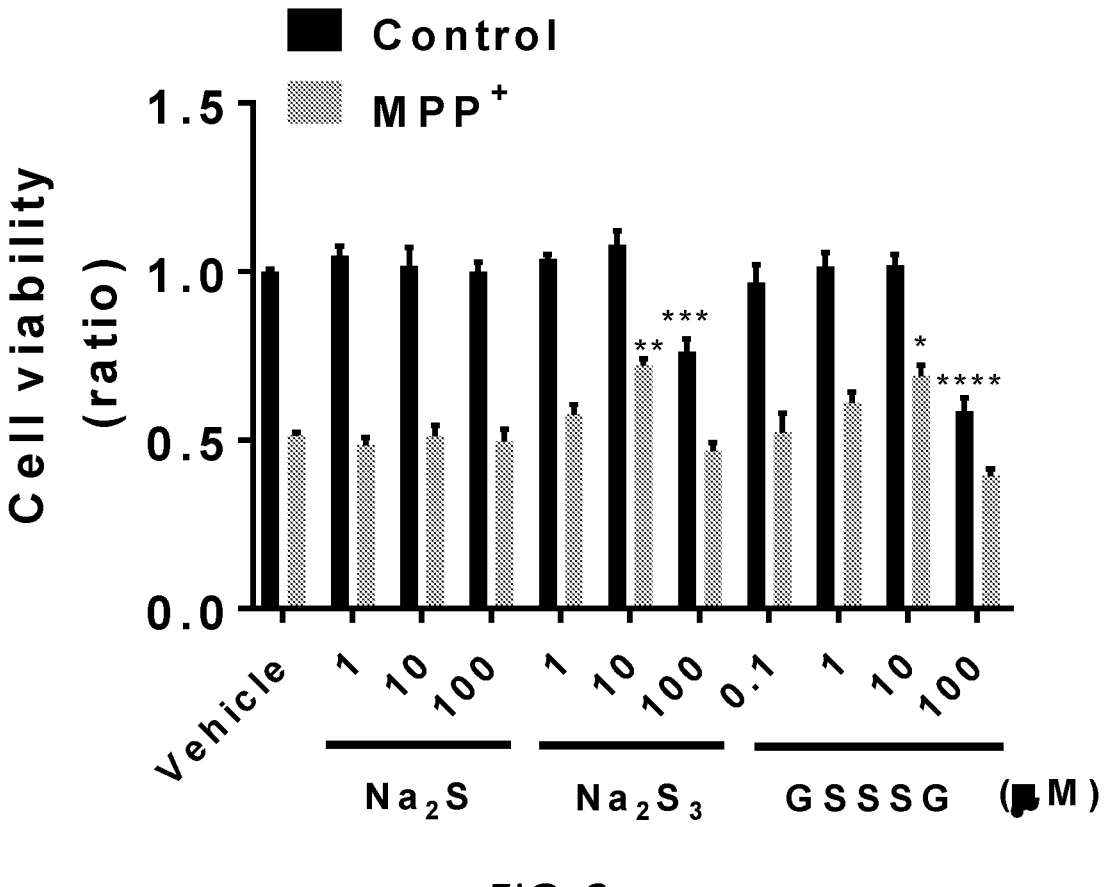
FIG. 2 is a graph showing that polysulfide, but not $Na_2S$, protected SH-SYSY cells from MPP+-induced cell death. N=4 each. *, , *, ****$P<0.05$, 0.01, 0.001, 0.0001 vs. vehicle; $P<0.01$ Control vs. MPP+ in each treatment.

The results, shown in FIG. 2, demonstrated that polysulfide, but not $Na_2S$, protected SH-SY5Y cells from MPP+-induced cell death.

REFERENCES CITED

Akaike, T., Ida, T., Wei, F.-Y., Nishida, M., Kumagai, Y., Alam, M. M., Ihara, H., Sawa, T., Matsunaga, T., Kasamatsu, S., et al. (2017). Cysteinyl-tRNA synthetase governs cysteine polysulfidation and mitochondrial bioenergetics. Nature Communications 8, 1177-1177.

Basso, D. M., Fisher, L. C., Anderson, A. J., Jakeman, L. B., McTigue, D. M., and Popovich, P. G. (2006). Basso Mouse Scale for locomotion detects differences in recovery after spinal cord injury in five common mouse strains. J Neurotrauma 23, 635-659.

Bell, M. T., Puskas, F., Agoston, V. A., Cleveland, J. C., Freeman, K. A., Gamboni, F., Herson, P. S., Meng, X., Smith, P. D., Weyant, M. J., et al. (2013). Toll-Like Receptor 4-Dependent Microglial Activation Mediates Spinal Cord Ischemia-Reperfusion Injury. Circulation 128, S152-S156.

Denes, A., Ferenczi, S., Halasz, J., Kornyei, Z., and Kovacs, K. J. (2008). Role of CX3CR1 (fractalkine receptor) in brain damage and inflammation induced by focal cerebral ischemia in mouse. J Cereb Blood Flow Metab 28, 1707-1721.

Donnelly, D. J., Longbrake, E. E., Shawler, T. M., Kigerl, K. A., Lai, W., Tovar, C. A., Ransohoff, R. M., and Popovich, P. G. (2011). Deficient CX3CR1 signaling promotes recovery after mouse spinal cord injury by limiting the recruitment and activation of Ly6Clo/iNOS+ macrophages. The Journal of neuroscience: the official journal of the Society for Neuroscience 31, 9910-9922.

Ida, T., Sawa, T., Ihara, H., Tsuchiya, Y., Watanabe, Y., Kumagai, Y., Suematsu, M., Motohashi, H., Fujii, S., Matsunaga, T., et al. (2014). Reactive cysteine persulfides and S-polythiolation regulate oxidative stress and redox signaling. Proceedings of the National Academy of Sciences.

Kakinohana, M., Kida, K., Minamishima, S., Atochin, D. N., Huang, P. L., Kaneki, M., and Ichinose, F. (2011). Delayed Paraplegia After Spinal Cord Ischemic Injury Requires Caspase-3 Activation in Mice. Stroke.

Kigerl, K. A., Lai, W., Rivest, S., Hart, R. P., Satoskar, A. R., and Popovich, P. G. (2007). Toll-like receptor (TLR)-2 and TLR-4 regulate inflammation, gliosis, and myelin sparing after spinal cord injury. Journal of neurochemistry 102, 37-50.

Ullery, B. W., Cheung, A. T., McGarvey, M. L., Jackson, B. M., and Wang, G. J. (2011). Reversal of delayed-onset paraparesis after revision thoracic endovascular aortic repair for ruptured thoracic aortic aneurysm. Ann Vasc Surg 25, 840 e819-823.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for the treatment, or reduction of risk, of a disorder associated with neurodegeneration in a subject, the method comprising administering a therapeutically or prophylactically effective amount of a composition comprising Glutathione Trisulfide (GSSSG) and saline to a subject in need thereof, wherein the disorder is post-ischemic neuronal death.

2. The method of claim 1, wherein the composition is prepared by dissolving a crystalline form of GSSSG in saline at pH 3-6.

3. The method of claim 1, comprising administering an effective amount of a composition comprising GSSSG and saline before a scheduled thoracic and/or abdominal aortic surgical procedure.

4. The method of claim 3, comprising administering an effective amount of a composition comprising GSSSG and saline hours to days before a scheduled thoracic and/or abdominal aortic surgical procedure.

5. The method of claim 4, comprising administering an effective amount of a composition comprising GSSSG and saline 2-24 hours, and/or 1, 2, 3, 4, 5, 6, and/or 7 days before the scheduled thoracic and/or abdominal aortic surgical procedure.

* * * * *